US005753227A

United States Patent [19]
Strahilevitz

[11] Patent Number: 5,753,227

[45] Date of Patent: May 19, 1998

[54] EXTRACORPOREAL AFFINITY ADSORPTION METHODS FOR THE TREATMENT OF ATHEROSCLEROSIS, CANCER, DEGENERATIVE AND AUTOIMMUNE DISEASES

[76] Inventor: Meir Strahilevitz, P.O. Box 190, Hansville, Wash. 98340

[21] Appl. No.: 97,378

[22] Filed: Jul. 23, 1993

[51] Int. Cl.$^6$ .................... A61K 39/00; A61M 37/00; B01D 15/08

[52] U.S. Cl. ............... 424/140.1; 210/638; 210/645; 210/646; 210/648; 210/651; 210/660; 210/661; 210/670; 210/688; 604/5; 604/6

[58] Field of Search .............. 424/140.1; 210/638, 210/645, 646, 660, 661, 688, 648, 651, 670; 604/5, 6

[56] References Cited

U.S. PATENT DOCUMENTS

| | | | |
|---|---|---|---|
| 3,453,194 | 7/1969 | Bennett et al. | 204/159.12 |
| 4,215,688 | 8/1980 | Terman et al. | 128/214 R |
| 4,228,015 | 10/1980 | De Vries et al. | 210/321 R |
| 4,375,414 | 3/1983 | Strahilevitz | 210/638 |
| 4,612,122 | 9/1986 | Ambrus et al. | 210/638 |
| 4,614,513 | 9/1986 | Bensinger | 604/6 |
| 4,627,915 | 12/1986 | Kuroda et al. | 210/195.2 |
| 4,637,880 | 1/1987 | Halbert | 210/638 |
| 4,714,556 | 12/1987 | Ambrus et al. | 210/638 |
| 4,737,544 | 4/1988 | McCain et al. | 604/5 |
| 4,813,924 | 3/1989 | Strahilevitz | 604/5 |
| 4,820,261 | 4/1989 | Schmoll et al. | 604/4 |
| 5,061,237 | 10/1991 | Gessler et al. | 604/5 |
| 5,091,091 | 2/1992 | Terman | 210/632 |
| 5,196,324 | 3/1993 | Bumol et al. | 435/70.21 |
| 5,258,503 | 11/1993 | Yokohari et al. | 604/5 |
| 5,474,772 | 12/1995 | Maddock | 424/140.1 |
| 5,626,843 | 5/1997 | Skurkovich et al. | 424/140.1 |

FOREIGN PATENT DOCUMENTS 8912390   12/1989   WIPO .

OTHER PUBLICATIONS

P. Aebischer et al., J. Biomech Eng., vol. 113 (2), 1991, pp. 178–183.
M. Amato et al., The International Journal of Artificial Organs, vol. 11 (3), 1988, pp. 175–180.
B.A. Bansal et al., Cancer, vol. 42, No.1, 1978, pp. 1–18.
R.E. Bird et al., Science, vol. 242, 1988, pp. 423–442.
H. Borberg et al., Journal of Clinical Apheresis, vol. 4, 1988, pp. 59–65.
T. Bratt and S. Ohlson, J. Clin. Lab. Immunol., vol. 27, 1988, pp. 191–195.
G. Brown et al., New England Journal of Medicine, vol. 323(19), Nov. 8, 1990, pp. 1289–1298.
E. Cranton, "Bypassing Bypass," Hampton Road Publishers, Norfolk, Virginia, 1992.
P.D.G. Dean et al., Ed., "Affinity Chromatography: A Practical Approach," IRL Press, Oxford 1985, pp. 1–73.
J. Goding et al., J.Immunological Methods, vol. 20, 1978, pp. 241–253.

C. Hartmann et al., Journal of Pharmacokinetics and Biopharmaceutics, vol. 19(4), 1991, pp. 385–403.
J.L. Held et al., Journal of American Academy of Dermatologists, vol. 28, 1993, pp. 253–254.
V. Hombach et al., Dtsch Med. Wschr, vol. 111(45), 1986, pp. 1709–1715.
R.A. Houghten, Proc. National Academy of Science USA, vol. 82, Aug. 1985, pp. 5131–5135.
D.J. King et al., Antibody, Immunoconjugates, and Radiopharmaceuticals, vol. 5(2), 1992, pp. 159–170.
T. Kita et al., Proceedings of the National Academy of Sciences USA, vol. 84, 1987, pp. 5928–5931.
J.W. Larrick, Pharmacological Reviews, vol. 41 No. 4, 1989, pp. 539–557.
J.L. Lear et al., Radiology, vol. 179, 1991, pp. 509–512.
R. Lindmark et al., J. Immunol. Methods, vol. 62, 1983, p. 1.
D.J. Lupien et al., Pediatric Res., vol. 14, 1980, pp. 113–117.
L. Marcus et al., American Heart Journal, vol. 110, No. 1, Part 1, Jul. 1985, pp. 30–39.
S.K. Mujais and P. Ivanovich, in "Replacement of Renal Function by Dialysis", Third Edition, Kluwer Academic Pub., J.F. Maher Editor, 1989, pp. 181–198.
K. Norrgren et al., Antibody Immunoconjugates and Radiopharmaceuticals, vol. 4(4), 1991, pp. 907–914.
A. Odaka et al., International Journal of Artificial Organs, vol. 9, 1986, pp. 343–348.
J.H. O'Keefe, Jr. and B.D. McCallister, Editorial, Mayo Clinic Proceedings, vol. 67, 1992, pp. 389–391.
E. Olszewer and J.P. Carter, Medical Hypotheses, vol. 27(1), Sep. 1988, pp. 41–49.
R.E. Ostlund, Jr., Artificial Organs, vol. 11(5), 1987, pp. 366–374.
J. Regnström et al., Lancet, vol. 339, No. 8803, May 16, 1992, pp. 1183–1186.
E.B. Rimm et al., New England Journal of Medicine, vol. 328(20), May 20, 1993, pp. 1450–1456.
J.T. Salonen et al, Lancet, vol. 339, No. 8798, Apr. 11, 1992, pp. 883–887.
J.T. Salonen et al., Circulation, vol. 86(3), Sep. 1992, pp. 803–811.
H. Savin et al., American Heart Journal, vol. 113(5), May 1987, pp. 1078–1084.

(List continued on next page.)

*Primary Examiner*—David Saunders
*Attorney, Agent, or Firm*—Polster, Lieder, Woodruff & Lucchesi

[57] ABSTRACT

Extracorporeal affinity adsorption treatments which are aimed at the substantial removal of two or more compounds that are etiological in the pathogenesis of diseases in man provide effective therapeutic intervention means for these diseases. The methods are particularly suitable for the treatment of atherosclerosis, cancer, degenerative and autoimmune diseases. Extracorporeal chelation and immunotherapy for atherosclerosis, extracorporeal chelation treatment with on-line regeneration or replacement of chelant, extracorporeal immunotherapy with antibody fragments, and extracorporeal immunoadsorption utilizing antibodies bound to Protein A are also disclosed.

62 Claims, 3 Drawing Sheets

OTHER PUBLICATIONS

D. Seidel et al., Journal of Clinical Apheresis, vol. 4, 1988, pp. 78–81.

R.D. Simari et al., Mayo Clinic Proceedings, vol. 67, Apr. 1992, pp. 317–322.

M.J. Stampfer et al., New England Journal of Medicine, vol. 328(20), May 20, 1993, pp. 1487–1489.

M. Strahilevitz, Atherosclerosis, vol. 26, 1977, pp. 373–377.

M. Strahilevitz, Lancet, vol. 340, Jul. 25, 1992, p. 235.

G.R. Thompson, Lancet, 1981 1, pp. 1246–1248.

A.M. Wallace and A. Wood, Clinical Chimica Acta, vol. 140, 1984, pp. 203–212.

G.W. Welling et al., Journal of Chromatography, vol. 512, 1990, pp. 337–343.

R.L. Wingard et al., American Journal of Kidney Diseases, vol. 18(5), 1991, pp. 559–565.

S.R. Wirebaugh and D.R. Gerates, DICP, vol. 24(1), Jan. 1990, pp. 22–24.

R. Yang et al., Antibody, Immunoconjugates and Radiopharmaceuticals, vol. 5, 1992, pp. 201–207.

S. Yokoyama et al., Arteriosclerosis, vol. 5, Nov./Dec. 1985, pp. 613–622.

*Mackh's Chemical Dictionary*, McGraw Hill, Inc., 1969, p. 148.

L. E. Hood et al, *Immunology*, Benjamin/Cummings Publishing Company, Inc., 1984, pp. 519–522.

I Schenkein et al, Jour. Clin. Invest., 50, 1864–1868, 1971.

EXTRACORPOREAL AFFINITY ADSORPTION METHODS FOR THE TREATMENT OF ATHEROSCLEROSIS, CANCER, DEGENERATIVE AND AUTOIMMUNE DISEASES

BACKGROUND OF THE INVENTION

Atherosclerosis and cancer are the two major causes of morbidity and mortality in western societies. While there has been significant advance in the treatment of atherosclerosis there is still a great need for more effective treatment interventions.

The main mechanism by which atherosclerosis leads to morbidity and mortality is by narrowing the lumen of arteries and reducing the blood supply to the heart, brain and other vital organs. The factors associated with atherosclerosis include: High levels of cholesterol, triglycerides, low density lipoproteins (LDL) and low levels of high density lipoproteins (HDL).

Other factors are heredity, cigarette smoking, obesity, high blood pressure, reduced physical activity, high fat diets, and a high oxidation activity associated with the production of free radicals, leading to the oxidation of LDL, which accelerates the development of atherosclerotic lesions. Thus, J. Regnström et al., Lancet, Vol. 339, No. 8803, May 16, 1992, pp. 1183–86, reported that the susceptibility of LDL to in vitro oxidation in the presence of copper, which acts as a catalyst in the oxidation process, was correlated with the severity of their coronary artery sclerosis. J. T. Salonen et al. Lancet, Vol. 339, No. 8798, Apr. 11, 1992, pp. 883–87, found that the level of autoantibodies to oxidized LDL predicted the progression of atherosclerosis of the carotid artery (the artery that supplies blood to the brain). One likely mechanism in development of atherosclerotic lesions via the oxidation of LDL is the induction of an autoimmune process leading to the production of antibodies specific to oxidized LDL and propagation of the atherosclerotic lesion by the autoantibody binding to oxidized LDL. J. Regnström et al., supra, and T. Kita et al., Proceedings of the National Academy of Sciences USA, Vol. 84, 1987, pp. 5928–31. J. T. Salonen et al., Circulation, Vol. 86(3), September 1992, pp. 803–11 reported an association between the risk of heart attack and the level of iron in the blood, with the risk being particularly high when plasma levels of both iron and LDL were elevated.

A significant reduction in blood levels of LDL and cholesterol by diet and lipid reducing drugs was found to result in regression of atherosclerosis. G. Brown, et al., New England Journal of Medicine, Vol. 323(19), Nov. 8, 1990, pp. 1289–1298. Oral lipid lowering drugs, such as Lovastatin, MSD (Mevacor®, Merck), are risky and may cause liver damage. Their efficacy is relatively limited, even when they are taken in association with a strict diet. Lowering of LDL by extracorporeal treatment of blood, M. Strahilevitz, U.S. Pat. Nos. 4,375,414 and 4,813,924, and M. Strahilevitz, Atherosclerosis, Vol. 26, 1977, pp. 373–77, is significantly more effective in reducing blood cholesterol and LDL levels. H. Borberg et al., Journal of Clinical Apheresis, Vol. 4, 1988, pp. 59–65; R. L. Wingard et al., American Journal of Kidney Diseases, Vol. 18(5), 1991, pp. 559–65; V. Hombach et al., Dtsch Med. Wschr, Vol. 111(45), 1986, pp. 1709–15. LDL and cholesterol can be removed by affinity adsorption, utilizing as the adsorbent antibodies to LDL or other specific chemical adsorbents, such as dextran sulphate (M. Odaka et al., International Journal of Artificial Organs, Vol. 9, 1986, pp. 343–48) or heparin (D. J. Lupien et al., Pediatric Res., Vol. 14, 1980, pp. 113–17). LDL removal can also be achieved by heparin precipitation (D. Seidel et al., Journal of Clinical Apheresis, Vol. 4, 1988, pp. 78–81), and by double filtration plasmapheresis (S. Yokoyama et al., Arteriosclerosis, Vol. 5, November/December 1985, pp. 613–22) as well as by plasma exchange (G. R. Thompson, Lancet, 1981 I, pp. 1246–48).

The oral administration of vitamin E is associated with lower risk of coronary heart disease in men (E. B. Rimm et al., New England Journal of Medicine, Vol. 328(20), May 20, 1993, pp. 1450–56) and in middle aged women (M. J. Stampfer et al., New England Journal of Medicine, Vol. 328(20), May 20, 1993, pp. 1487–89). The mechanism of this protective effect is based on the antioxidant property of vitamin E, which inhibits the oxidation of LDL, thus exerting a protective effect from the development of atherosclerosis. The oxidation of LDL is catalyzed by heavy metals such as iron and copper. The removal of the metals by intravenous administration of chelating agents was reported to be effective in atherosclerotic vascular disease. E. Olszewer and J. P. Carter, Medical Hypotheses, Vol. 27(1), September 1988, pp. 41–49, and E. Cranton, "Bypassing Bypass," Hampton Road Publishers, Norfolk, Va., 1992. Others did not confirm these reports. S. R. Wirebaugh and D. R. Gerates, DICP, Vol. 24(1), January 1990, pp. 22–24.

The apparent minimal effect, or lack of effect, of intravenous chelation in the treatment of atherosclerosis can be overcome by extracorporeal chelation which significantly increases chelation efficacy and reduces significantly its toxicity. M. Strahilevitz, Lancet, Vol. 340, Jul. 25, 1992, p. 235.

Extracorporeal chelation with desferoxamine was highly effective and safe in reducing blood iron in the treatment of hemochromatosis, a disease caused by the accumulation of excess iron in the blood and body stores. J. L. Held et al., Journal of American Academy of Dermatologists, Vol. 28, 1993, pp. 253–54. Ambrus and Horvath in U.S. Pat. No. 4,612,122 also describe a specific column configuration that can be used for extracorporeal chelation. In this column the chelating agent is physically immobilized in the spongy outer part of an anisotropic (asymmetrical) membrane.

Chelating agents can also be utilized with the extracorporeal affinity adsorption devices of Strahilevitz, U.S. Pat. No. 4,375,414.

Coronary bypass surgery is effective in reducing symptomatology, but its effect on mortality is limited. J. H. O'Keefe, Jr. and B. D. McCallister, Editorial, Mayo Clinic Proceedings, Vol. 67, 1992, pp. 389–91, R. D. Simari et al., Mayo Clinic Proceedings, Vol. 67, April 1992, pp. 317–22.

Bypass surgery has no curative effect on the atherosclerotic disease process. The problem of post surgery atherosclerosis progression and the development of coronary or graft restenosis are major problems associated with bypass surgery. The need for effective means for reducing progression and inducing regression of atherosclerosis in patients following bypass surgery is well recognized, as is the need to further develop effective nonsurgical treatments that would replace bypass surgery in a significant proportion of patients that are currently being treated with bypass surgery, because of the lack of alternative effective medical treatment.

This is particularly relevant for candidates for bypass coronary surgery with moderately severe coronary occlusion that may not exhibit significant fibrotic changes in the atherosclerotic coronary lesions. Similar limitations to those of bypass surgery apply to percutaneous transluminal coronary angioplasty. Simari et al., supra. In this procedure, an inflatable balloon is inserted into the coronary occlusion site. As with bypass surgery, this procedure also has no effect on the atherosclerotic disease process, thus restenosis is a significant problem. While the risks associated with angioplasty are lower than with bypass surgery, this is also an invasive procedure associated with morbidity and mortality risks.

While current medical treatments, particularly when combinations of conventional treatments are utilized, have significant effect in reducing progression and in inducing regression of the atherosclerotic process (Brown et al., supra), there is a need to have more effective treatment methods, particularly for those who can not be treated with oral lipid lowering drugs because of liver toxicity, who are unable to maintain a strict diet, or who fail to improve with conventional treatment, including oral lipid lowering drugs and diet.

The utilization of extracorporeal affinity adsorption of LDL (Strahilevitz, supra) can lead to marked reduction in LDL level, thus to significant regression of atherosclerotic coronary lesions. Hombach et al., supra. However, the effect of affinity adsorption of LDL and cholesterol, while aimed at a major factor in atherosclerosis, hyperlipidemia, is selectively targeted on this factor. Even when (as usually is the case) the affinity LDL adsorption is utilized with other measures (diet, exercise etc.) the quantitative impact of these conventional treatment methods may not be sufficient. The availability of non-surgical methods that will have a significantly larger quantitative effect on additional factors that are involved in the etiology and pathogenesis of atherosclerosis is of great importance, in order to optimize the non-surgical and post-surgical treatment of atherosclerosis.

SUMMARY OF THE INVENTION

One of the objects of the present invention is to provide effective non-surgical treatments of atherosclerosis.

Another object is to provide improvements in extracorporeal treatment methods for atherosclerosis and other diseases.

Another object is to provide improved specific affinity devices, particularly immunoadsorption devices, and methods.

Other objects will become apparent to those skilled in the art in light of the following description.

In accordance with one aspect of the present invention, methods for treating atherosclerosis are provided that are based on the utilization of specific affinity adsorption of several of the biological molecules that are etiological in the pathogenesis of atherosclerosis. The affinity adsorbents utilized in accordance with the present invention are both immunoadsorbents and non-immune-based specific affinity chemical adsorbents.

In some applications of extracorporeal combined treatment, one or both of the extracorporeal methods may be based on other principles than adsorption, for example use of extracorporeal double filtration for the removal of LDL. S. Yokoyama et al., supra.

The adsorbents are incorporated in an extracorporeal treatment device. The methods of the present invention will be usually utilized in conjunction with conventional treatment methods, both medical and, when indicated, surgical methods.

The novel treatment methods that are the subject of the present invention are based on and are specific improvements of extracorporeal affinity adsorption and extracorporeal affinity dialysis which are disclosed in Strahilevitz U.S. Pat. Nos. 4,375,414 and 4,813,924 and British provisional patent application No. 16001, May 20, 1971 which are incorporated herein by reference.

It is one of the objects of the present invention to provide additional specific improvements and embodiments to further increase the effectiveness and utility of extracorporeal affinity adsorption treatment of atherosclerosis.

Many of the elements of the present invention, as it applies to the treatment of atherosclerosis, are discussed in M. Strahilevitz, Lancet, Vol. 340, Jul. 25, 1992, p. 235, which is incorporated herein by reference.

One aspect of the present invention is to provide novel extracorporeal treatments for atherosclerosis based on specific affinity adsorption. The present invention also improves the efficacy of extracorporeal LDL affinity adsorption by combining it with affinity adsorption of ligands other than LDL and other lipids, that are also etiological in atherosclerosis.

Another aspect of the present invention is providing means for reducing the level of oxidized LDL in the body, using as affinity adsorbents specific antibodies to oxidized LDL, or using as specific adsorbent enzymatic digestion fragments of such antibodies, or synthetic fragments of such antibodies.

Yet another aspect of the invention is improving the immunoaffinity adsorption of LDL through the utilization of specific synthetic fragments of antibody (G. W. Welling et al., Journal of Chromatography, Vol. 512, 1990, pp. 337–43), with synthetic fragments that are specific to LDL. Yet another aspect is providing means for extracorporeal affinity adsorption of autoantibodies to oxidized LDL, which may be etiological in atherosclerosis, by using as the specific adsorbent oxidized LDL (the antigen) such as malondialdehyde LDL (Salonen, Lancet, supra), or to use as the adsorbent of oxidized LDL autoantibodies, Staphylococcal Protein A (Strahilevitz, Lancet, supra). Rather than Staphylococcal Protein A, a recombinant Staphylococcal Protein A or Staphylococcal Protein A component, or other synthetic peptides of Staphylococcal Protein A may be utilized, as may Protein G or its components. Bensinger, U.S. Pat. No. 4,614,513; R. Lindmark et al., J. Immunological Methods, Vol. 62, 1983, p. 1. As used herein, except when the context clearly indicates otherwise, the terms "Protein A" and "Protein G" include all such variations.

When fragments of antibodies are used in the present invention as affinity adsorbents, they can be produced by enzymatic (e.g., papain or pepsin) digestion of the intact antibody to produce Fab, (Fab')2, or FV antigen-binding fragments, or they can be produced by other methods known to those skilled in the art for the synthesis of peptides, such as solid phase synthesis (R. A. Houghten, Proc. National Academy of Science USA, Vol. 82, August 1985, pp. 5131–35; R. E. Bird et al., Science, Vol. 242, 1988, pp. 423–42) or through genetic engineering in a suitable vector such as *E. coli* or phage (J. W. Larrick, Pharmacological Reviews, Vol. 41(4), 1989, pp. 539–57). The use of fragments, rather than intact antibodies, as the affinity adsorbent may increase the adsorption capacity and reduces side effects that may be associated with the Fc non-antigen binding part of the antibody molecule.

Another objective of the invention is to provide for extracorporeal chelation therapy for cancer, autoimmune diseases and degenerative diseases, such as rheumatoid arthritis.

An additional objective is to provide extracorporeal combined treatment of cancer based on combining extracorporeal chelation and extracorporeal adsorption of enhancing tumor antibodies and their complexes by utilizing one or more of the following specific adsorbents, (a) Tumor specific antigen and (b) Staphylococcal Protein A or Protein G.

DESCRIPTION OF THE PREFERRED EMBODIMENTS

The following are examples of the preferred embodiments of devices and methods of the present invention. All of the examples utilize selective affinity binding of one ligand to another. The ligand which is held in an extracorporeal device will be referred to herein as a specific affinity "adsorbent," even in cases in which that ligand is in solution or suspension, and the process of binding a chemical species carried in a fluid by means of the specific affinity adsorbent will be referred to as "affinity adsorption."

Affinity Filtration Chelation

Figure 1:
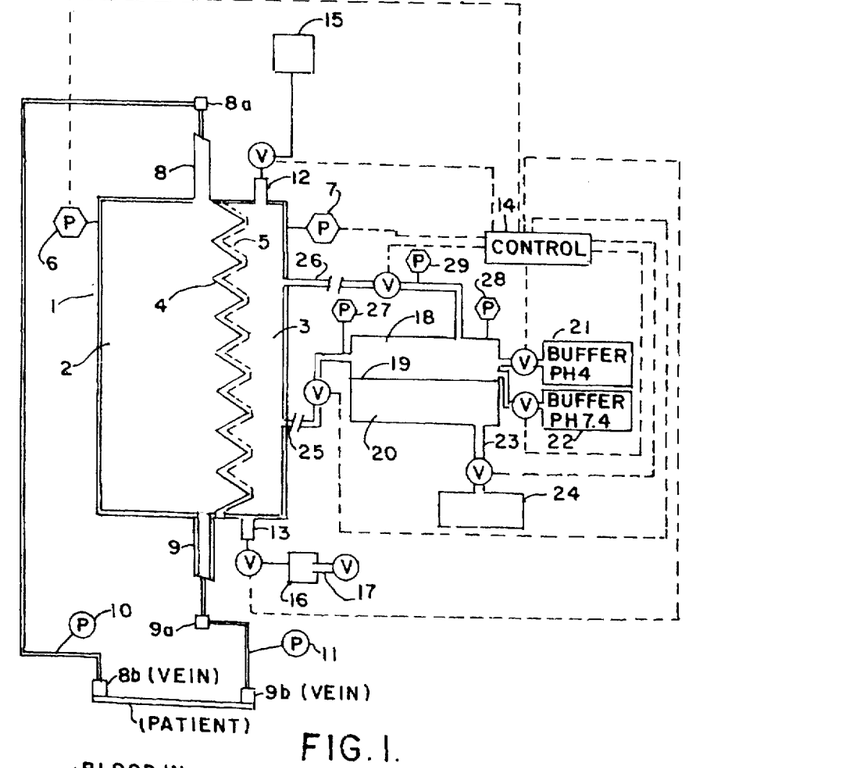
FIG. 1 is a diagrammatic view illustrating an affinity filtration device utilized for extracorporeal chelation therapy in accordance with the present invention.

Referring now to the drawings, and in particular to FIG. 1, an apparatus is provided which corresponds to the apparatus of my U.S. Pat. No. 4,375,414, but in which a chelating agent is utilized as the specific affinity adsorbent. A column 1 is divided into a first compartment 2 and a second compartment 3, by a semipermeable membrane 4. Such membranes having various pore sizes and which are permeable to molecules of molecular weight below a particular weight only ("cut off") are available commercially. Preferred is a membrane with a pore size of 0.001 micron to 0.01 micron, a suitable molecular weight cut off is 1,000 to 10,000 daltons. One suitable membrane is a polysulphone membrane (M. Amato et al., The International Journal of Artificial Organs, Vol. 11 (3), 1988, pp. 175–80. Another suitable membrane is made of modified Cuprophan (Hemophan). (S. K. Mujais and P. Ivanovich in "Replacement of Renal Function by Dialysis", Third Edition. Kluwer Academic Pub., J. F. Maher Editor, 1989, pp. 181–98.

The membrane is preferably pleated to increase its surface area. The membrane is mechanically supported by a rigid mesh screen 5, facing compartment 3, thus avoiding contact of the mesh support material with the blood flow. Positive pressure pump 6 and negative pressure pump 7 are connected to compartments 2 and 3 and can be optionally operated when increased pressure across the membrane is needed for enhancing the mass transfer across the membrane between compartments 2 and 3. The overall surface area of the membrane is between 0.5 m²–3 m². The pumps are connected to a control 14 to enable automatic operation. Compartment 2 has an inlet 8 for a catheter 8a, which is to be connected to a vein 8b of the patient (when vein to vein connection is used, which is the preferred operation). Catheter 8a may however be connected to an artery of the patient when desired. Outlet 9 is connected to a catheter 9a, which is to be connected to another vein 9b of the patient. Together they comprise a blood flow passage through compartment 2. The second compartment 3 includes the chelating agent. Preferably the chelating agent is a multivalent chelating agent such as a biotechnology grade resin marketed by Biorad Corp. under the registered trademark Chelex 100. This resin is a styrene divinylbenzene copolymer containing paired iminodiacetate ions, which act as chelating groups for binding polyvalent metal ions. Chelation is based on coordination binding between the chelating agent and the heavy metals, which is similar to a covalent bond, but in which both electrons are donated by the same atom. Chelating binding differs from ion exchange by its high selectivity for heavy (transition) metal ions and by its much higher bond strength. Chelex 100 resin has the following selectivity for some cations (a higher number indicates greater affinity): $Hg^{++}=1060$, $Cu^{++}=126$, $Na^{+}=1\times10^{-7}$.

The Chelex 100 resin is obtained in 200 mesh size and is ground to particles with a diameter of 5 to 30 microns. The dialysis fluid is a standard renal dialysis fluid, preferably bicarbonate type buffered to pH 7.4.

While Chelex 100 is preferred for some applications, other chelating agents can be used when bound to macromolecular organic or inorganic particles, such as triaminepenta acetic acid or deferoxamine bound to a suitable matrix, such as silica. Other chelating agents are derivatives of iminodiacetic acid such as EDTA and matrix bound glycine hydroxamic acid.

Peristaltic pumps 10 and 11 are optional and may be used as needed to accelerate blood flow into and out of compartment 2. The blood flow through the device is in the range of 25 ml to 250 ml per minute. The system described thus far can be used without on-line regeneration, with the replacement of buffer and chelating agent as needed via inlet 12 and outlet 13. This mode of treatment can be operated manually or automatically, by the use of control 14 to operate the valving of inlet 12 and outlet 13, in conjunction with reservoir 15 that contains fresh Chelex dialysis fluid suspension. Reservoir 16 collects "used up" Chelex with its chelated heavy metals. Drain 17 can be used to clear reservoir 16, for discarding, chemical analysis or off line regeneration of the chelating agent.

Optionally, the system can operate with either manual or automatic on-line regeneration of the chelating agent. The automatic regeneration is identical to Strahilevitz, U.S. Pat. Nos. 4,375,414 and 4,813,924, except for the use of a buffer pH 4 rather than pH 2.5.

Because the chelating agent specifically binds heavy metals such as $Cu^{++}$ and $Fe^{++}$ that are mass transferred across the membrane barrier, a continuous gradient is present for the heavy metals that continue to mass transfer from compartment 2 to compartment 3 across membrane 4 by diffusion and/or convection, as long as compartment 3 contains free chelating groups that are available to bind heavy metals. When pressure filtration is utilized, by operating the optional positive pressure pump 6 and/or negative pressure pump 7, the process of mass transfer is accelerated by increased convection.

Optional means are provided for on-line continuous regeneration of the chelating agent. Preferably regeneration is achieved by use of a weak acid solution at pH 4 or higher. However, elution can also be achieved by use of a concentrated salt solution, or by the use of a low molecular weight free chelator, such as EDTA (specific elution). When on-line regeneration is used, the Chelex bound heavy metals buffer solution is transferred through outlet 25 to compartment 18 with optional operation of peristaltic pump 27. The buffer is pressure filtered through membrane 19 to compartment 20 (permeable to the buffer but not to the Chelex). The positive pressure for filtration is provided by pump 28. The elution (regeneration) buffer is then transferred from compartment 21 to compartment 18 and again positive pressure pump 28 transfers the heavy metals eluted from the Chelex to compartment 20 and through outlet 23 to compartment 24, from which it can be discarded or used for chemical analysis. Buffer pH 7.4 is added from reservoir 22 to compartment 18 and the regenerated Chelex is returned to compartment 3 via conduit 26. Optional peristaltic pump 29 is used to accelerate transfer. Alternatively, other configurations can be used for on-line regeneration, such as the one utilized in S. P. Halbert, U.S. Pat. No. 4,637,880.

While the method described thus far uses Chelex with beaded, preferably regular spherical, form, other forms of matrix can be used such as irregular beads or fibers, either natural or synthetic, to which the chelating moiety can be covalently bound or physically trapped (immobilized).

The chelating moiety can also be covalently bound to semipermeable membrane 4, when the membrane is made of synthetic polymer or from natural or modified polymer. The binding can be to the membrane side facing the blood flow, the membrane side facing the dialysis chelator flow, or to both sides. The physical configuration of the matrix is not limited to any particular form, as long as the matrix configuration and its particle size prevents the chelating agent from being substantially transferred from compartment 3 to compartment 2.

The affinity chelation filtration can be utilized for affinity adsorption of a plurality of ligands, for example when free antibodies or antibodies bound covalently to a matrix or polymerized antibodies are included in compartment 3 and semipermeable membrane 4 is permeable to the antigen or hapten to which the antibodies are specific. An example for such antibodies are the antibodies to free cholesterol.

Affinity Adsorption Chelation

The configuration and process of this treatment is similar to affinity filtration chelation, except that the semipermeable membrane 4 and its mesh screen membrane support are excluded from the device of FIG. 1, along with pumps 6 and 7. A chelating agent, Chelex 100, ground to particle size of between 1–5 microns is encapsulated in a suitable microcapsule or macrocapsules. The macrocapsules used are those utilized by A. M. Wallace and A. Wood, Clinical Chimica Acta, Vol. 140, 1984, pp. 203–12, for encapsulating antibodies and have an average diameter of 30 microns, or they are thermoplastic based macrocapsules (P. Aebischer et al., J. Biomech. Eng., Vol. 113 (2), 1991, pp. 178–83) having a diameter of 560±65 microns. Another suitable encapsulation of Chelex is by modification of the method of L. Marcus et al., American Heart Journal, Vol. 110, No. 1, Part 1, July 1985, pp. 30–39. The method used by Marcus et al. involved encapsulation of anti-digoxin antibodies in 0.2 micron polyacrolein microspheres, which are then encapsulated in 500–800 micron cross-linked agarose macrospheres. For encapsulation of Chelex, the Chelex is directly encapsulated in the cross-linked agarose macrospheres omitting the polyacrolein microencapsulation. Marcus et al. used their encapsulated antidigoxin antibodies in a column for extracorporeal adsorption treatment of digitalis intoxicated dogs. The same treatment was used in digitalis intoxicated humans. H. Savin et al., American Heart Journal, Vol. 113(5), May 1987, pp. 1078–84.

When Chelex is used in free form, particles of about 30 to 300 microns are preferred. Other matrixes and other chelating agents bound to the matrixes can be used. The matrixes can be of various chemical composition including, for example: natural polymers such as cellulose and dextran; various synthetic polymers and copolymers such as polyacrylamide, polystyrene, and polyvinyl polystyrene copolymer, and glass and silica. One suitable matrix is heparinized silicone described in D. R. Bennett et al., U.S. Pat. No. 3,453,194. Various matrixes and methods for their activation for covalent ligand binding are described in P. D. G. Dean et al., Editors "Affinity Chromatography: A Practical Approach," IRL Press, Oxford 1985, pp. 1–73. The configuration of the matrix is also not limited to a particular form; examples of suitable forms are beads (in particular, spherical in shape), fibrous matrixes, macroporous matrixes, and membranes including hollow fibers.

One possible configuration of the device is that of a typical multi-hollow fiber dialyzer or diafilter design. Such a design consists of a bundle of hollow fibers encased in a tubular housing.

Figures 2, 3:
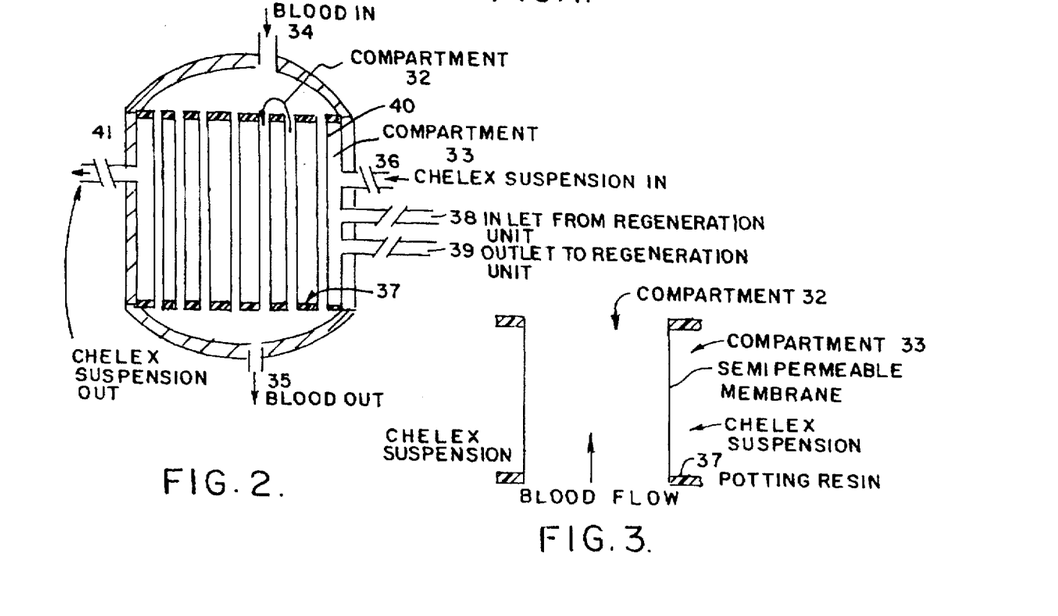
FIG. 2 is a multi-hollow fiber dialyzer or diafilter utilized for extracorporeal chelation therapy in accordance with the present invention.
FIG. 3 is a detail of one hollow fiber of the device of FIG. 2.

In this configuration compartment 2 corresponds to the inner space of the hollow fibers and compartment 3 to the outer space of the hollow fibers.

In FIG. 2, blood flows from patient's vein through inlet 34 to compartment 32 (inner space of fibers). Heavy metals which pass across semipermeable membrane 40 are bound by chelation to Chelex suspended in compartment 33. The blood that flows out through outlet 35 is connected to another vein of the patient. This blood is relatively free from heavy metals. Inlet 36 is used to replace used up Chelex suspension with new Chelex suspension. The old Chelex suspension is drained through drain 41. This step is optional. Optionally also, Chelex may be regenerated online by the same online regeneration means described with respect to FIG. 1. "Used up" Chelex suspension is transferred from compartment 33 through outlet 39 to the regeneration unit. Regenerated Chelex suspension is returned to compartment 33 from the regeneration unit through inlet 38. Suitable pumps may be utilized if it is desirable to increase the blood pressure in compartment 32 and across membrane 40, thus increasing the rate of mass transfer from compartment 32 to compartment 33 by a filtration process.

The space between fibers is sealed by sealing resin 37.

FIG. 3 illustrates a single fiber in the unit. A typical fiber's membrane thickness is 6–30 microns. The combined inner membrane surface area is typically 0.75 to 1.2 meter$^2$.

Commercially available dialysers that can be used are Fresenius model F60 or Asahi PAN 150.

Figure 4:
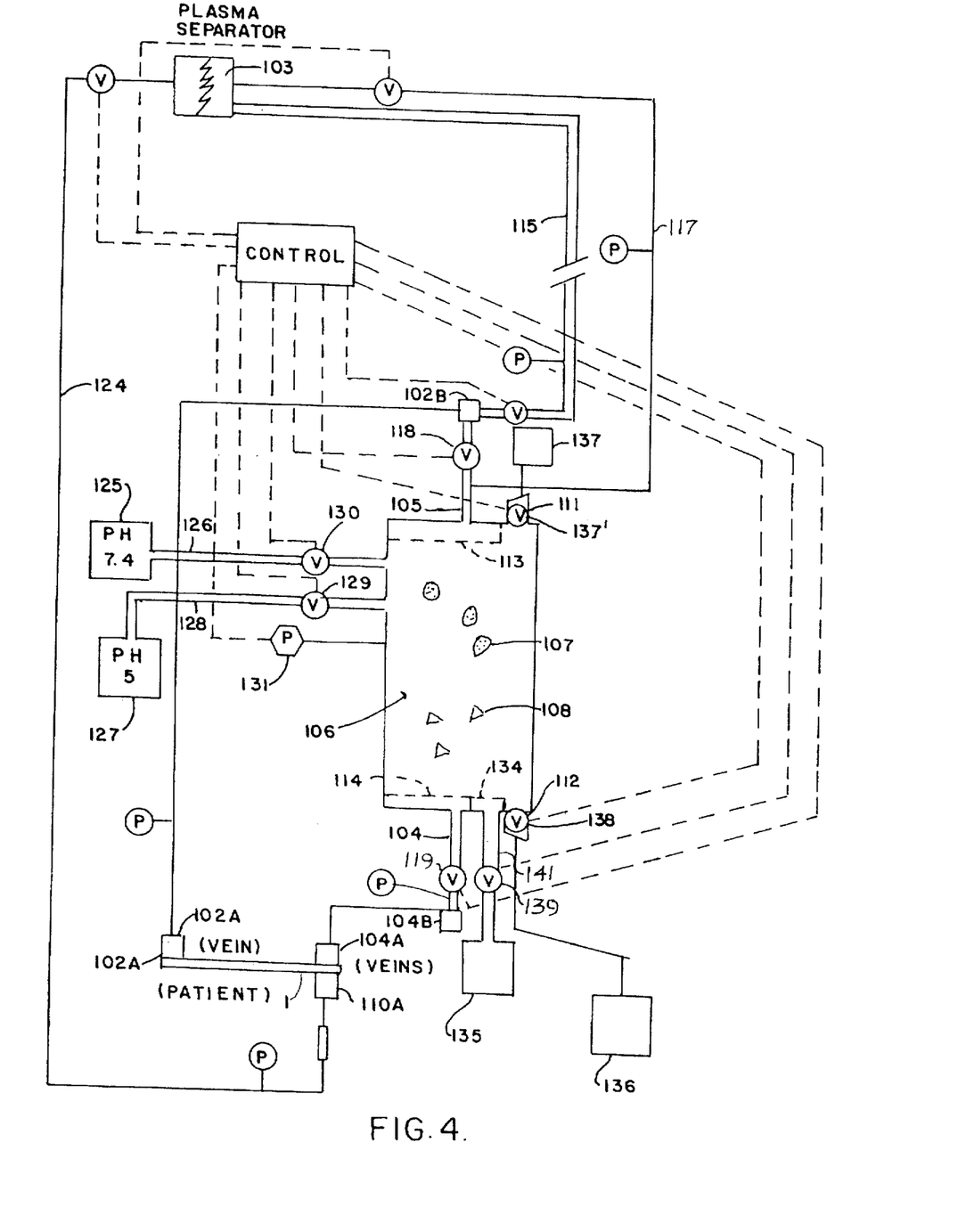
FIG. 4 is a diagrammatic view of an extracorporeal affinity adsorption device for use with the present invention.

Another embodiment of affinity adsorption device for use in the present invention is shown in FIG. 4. The device of FIG. 4 can be used to treat either blood or plasma. Particularly suitable for direct blood treatments are devices in which the matrix-bound chelator is encapsulated or when the matrix is a spiral structure such as for example natural polymer or synthetic polymer membrane to which the chelating moiety is covalently bound. When plasma is treated in the device, a plasma separator is first used to separate on-line the patient's plasma from the cellular elements of blood. The physical configurations may include beads, in particular spherical beads, fibers, macroporous matrixes, membranes, and hollow fibers.

Blood may be directly treated, preferably when the matrix bound chelator is encapsulated. If plasma is treated, then the patient's blood flows via conduit 115 to plasma separator 103 (e.g., a centrifugal continuous plasma separator such as marketed by Cobe (Cobe IBM 2997) or preferably a membrane filtration plasma separator such as Kaneka Sulfox or Cobe TPE). The blood cells are returned to the patient via conduit 124 and the plasma is passed through conduit 117, via inlet 105 to column 106.

When encapsulation of matrix chelate is not utilized in the system and the method utilizes treatment of plasma, on-line manual or automatic regeneration can be used using a modification of the methods of Strahilevitz, U.S. Pat. No. 4,813,924 or the method of Halbert, U.S. Pat. No. 4,637,880.

In the on-line regeneration mode, with inlets 105 and 111 closed, outlet 112 to reservoir 136 closed, and either valve 119 or valve 139 closed, valve 130 is opened and buffer pH 7.4 is transferred from reservoir 125 to column 106. This is an optional step utilized when it is desirable to wash some of the patient's plasma that is present in column 106 into the patient's circulation (with valve 119 open) or to drain this washed volume of plasma through drain 141. This is done when it is desirable to reduce the amount of plasma proteins that is exposed to the eluting buffer. A small volume of buffer pH 7.4 is used, in order to minimize the volume of buffer introduced into the patient, when the option of returning the plasma to the patient is used. Alternatively the removal of plasma from column 106 back to the patient, can be accelerated by using positive pressure filtration with operation of pump 131.

In the elution step, with all valves except valves 129 and 139 closed, eluting buffer pH 5 is transferred to column 106 from reservoir 127; after equilibration, valve 129 is closed, valve 139 is opened and the buffer, including the free heavy metal cations passes through drain 141. Optionally, pressure filtration can be utilized with operation of pump 131. Optional filter 134 is permeable to buffer, heavy metal cations, and plasma proteins about the size of LDL, but not to Chelex and plasma proteins larger than LDL; the drained fluid is then collected in reservoir 135 and can be discarded or used for chemical analysis. In the next step column 106 is equilibrated with buffer pH 7.4, transferred from reservoir 125 through conduit 126.

When on-line regeneration is not used, replacement of used adsorbent by fresh adsorbent can be done manually, or automatically by automatic control of valves 137' and 138 with addition of fresh adsorbent from reservoir 137 and collecting used adsorbent in reservoir 136.

Column 106 is then ready for re-use. Preferably vein to vein catheterisation is used, but when needed artery to vein catheterisation is utilized. When needed peristaltic pumps are used to accelerate fluid and mass transfer across the conduits 104, 105, 115, 117, 124 and 141.

The affinity adsorption method is well adapted to the concurrent adsorption of a plurality of ligands. On-line regeneration can be used when needed, and is particularly simple when the regeneration of the various adsorption ligates can be regenerated by the same regeneration means, such as by an acidic pH buffer, for example. The various adsorbents can be present in free form or can be encapsulated in microcapsules. Free form adsorbents are preferable because of their mechanical strength and suitability for regeneration, when desired. Encapsulated adsorbents will generally not be suitable for regeneration.

In FIG. 4, column 106 contains a first adsorbent 107 and a second adsorbent 108. Illustratively, the first adsorbent 107 is Chelex 100 in bead form, with a bead diameter in the range of 5 to 30 microns when encapsulated and 30 to 300 microns when free. The bead is preferably in free form, but can be encapsulated as previously described. The microcapsule membrane, when present, is permeable to heavy metals but not to Chelex or to plasma proteins. The Chelex specifically adsorbs heavy (transition) metals which catalyze oxidation of LDL. The second adsorbent 108 is cyanogen bromide activated cross-linked agarose (Sepharose, Pharmacia Fine Chemicals), with a bead diameter in the range of 212–300 microns, prepared according to R. E. Ostlund, Jr., Artificial Organs, Vol. 11(5), 1987, pp. 366–74. The Sepharose is covalently bound to monoclonal antibodies to LDL. (R. L. Wingard et al., supra). According to Ostlund, supra, LDL is adsorbed by the antibodies. As previously described, rather than intact antibodies, antibody fragments can be used. The combined effects of significant reductions of both oxidation and LDL levels have a major impact on the atherosclerotic process.

Plasma which flows from column 106 though outlet 104 is substantially free of the species sought to be removed. Drains 111 and 112 can be used as needed for the removal of buffer and binding species, and for the addition of fresh binding species. Used binding species (e.g., anti-LDL antibodies and Chelex) can be regenerated off line, if needed. It should also be recognized that antibodies or fragments, "humanized" or hybrid antibodies (or fragments) can be used rather than mouse antibodies. J. W. Larrick, supra. In synthesizing antibody fragments, solid phase peptide synthesis methods (R. A. Houghten, supra) or genetic engineering methods (R. E. Bird et al., supra) can be utilized.

The advantage of Ab fragments over intact antibody is the reduced likelihood of side effects of the immunoadsorption treatment, particularly when whole blood is used for adsorption and the antibody or fragment is not encapsulated thus enabling contact of the mouse antibody with the patient's immune cells.

Additional adsorbents that can be utilized in the treatment of atherosclerosis include oxidized LDL, which will adsorb autoantibodies to oxidized LDL (cf. Salonen et al., Lancet, supra; Strahilevitz, Lancet, supra). Instead of the oxidized LDL, autoantibodies to oxidized LDL and their complexes can be adsorbed by use of Sepharose 4BCL Protein A, sold by Pharmacia Fine Chemicals. When Protein A is used as the adsorbent, the patient may need administration of replacement human gamma globulin. Additionally it may be desirable to adsorb oxidized LDL by using matrix bound antibodies to oxidized LDL as the adsorbent.

When affinity adsorption is used in accordance with the present invention for the adsorption of antigens or haptens, such as adsorption of LDL or oxidized-LDL in the treatment of atherosclerosis or adsorption of rheumatoid factor (autoantibodies to Human IgG) in the treatment of rheumatoid arthritis, for example, the application of the analytical method of J. Goding et al., J. Immunological Methods, Vol. 20, 1978, pp. 241–53, to extracorporeal affinity adsorption in accordance with the present invention, is a general method for the removal of antigens or haptens from the body. It should be clearly realized that any antigen or hapten can be removed from the body in accordance with this invention. In accordance with this method first Protein A or genetically engineered Protein A peptide (R. Lindmark et al., supra) is covalently bound to any of the matrixes described in the current invention, for example Sepharose 4BCL. The antibody specific to the antigen, for example monoclonal antibody specific to LDL, is added to the Sepharose-bound Protein A. It binds to Protein A through its Fc part, and its Fab antigen binding part is available to bind the antigen (LDL). The matrix bound Protein A-LDL-antibody is incorporated in the extracorporeal immunoadsorption (affinity adsorption) treatment column as described in the foregoing examples, for the treatment of atherosclerosis. Clearly it is possible to use Protein G instead of Protein A in this system.

When larger beads of cross linked Sepharose are used as matrix, they are prepared according to Ostlund, supra.

In the treatment of cancer the affinity adsorbents can include for example: Chelex 100 to reduce oxidation and Staphylococcal Protein A, or tumor specific antigens to remove enhancing tumor antibodies and their complexes.

An additional component of the combined treatment is to administer a radioactive drug or conventional drug conjugated to an antibody specific to a tumor antigen (such as Adriamycin conjugated to an antibody to Human-Alpha-Fetoprotein. R. Yang et al., Antibody, Immunoconjugates and Radiopharmaceuticals, Vol. 5, 1992, pp. 201–07), in conjunction with adsorption of the antibody-drug conjugate from blood. K. Norrgren et al., Antibody Immunoconjugates and Radiopharmaceuticals, Vol. 4(4), 1991, pp. 907–14.

The utilization of tumor-targeted radiolabeled antibody in conjunction with immunoadsorption of the radiolabeled antibody from the circulation to improve tumor imaging was reported by J. L. Lear et al., Radiology, Vol. 179, 1991, pp 509–12. The adsorbent they used was an antibody to the radiolabeled anti-tumor antibody. The adsorbing antibody was utilized in an extracorporeal column in which it was covalently bound to a matrix. C. Hartmann et al., Journal of Pharmacokinetics and Biopharmaceutics, Vol. 19(4), 1991, pp. 385–403, evaluated the removal of radiolabeled antibody by extracorporeal adsorption, also using antibody to the radiolabeled antibody as the adsorbent. They found that the method would be effective for enhancing tumor imaging and for increasing the efficacy and reducing the toxicity of antibody-targeted anti-tumor drugs. These authors also cite two additional groups reporting similar results.

In accordance with the present invention, the anti-tumor drug or radiolabeled anti-tumor antibody is adsorbed in an extracorporeal column utilizing Staphylococcal Protein A as the adsorbent. This is a simpler and less expensive adsorbent and has the additional advantage of adsorbing enhancing antibodies and immune complexes; this enhanced removal has an important therapeutic effect on cancer. As previously mentioned, when Protein A is used as the affinity adsorbent, it may be necessary to administer intravenously, to the subject being treated, plasma or a plasma constituent such as gamma globulin.

It should be clearly understood that in enhancing tumor imaging utilizing antibody-targeted radioactive ligand, as disclosed in Hartmann et al., supra, Lear et al., supra, or Norrgren et al., supra, Protein A or Protein G can be utilized as the adsorbents.

Moreover, the radioactive imaging ligand may be incorporated in a hapten or antigen, preferably conjugated to the targeting antibody (or antibody fragment) by a spacer arm. The affinity adsorbent may then be an antibody to the free hapten or antigen, and all of the methods discussed above for binding drugs bound to targeting antibodies may be utilized. Engineered targeting antibody fragments are disclosed in D. J. King et al., Antibody, Immunoconjugates, and Radiopharmaceuticals, Vol. 5(2), 1992, pp. 159–70.

In the treatment of cancer the adsorption treatment will also be combined with conventional therapy such as chemotherapy.

Circulating immune complexes can also be adsorbed by C1q subcomponent of complement bound to specific antibodies to C1q, which are covalently bound to the matrix. T. Bratt and S. Ohlson, J. Clin. Lab. Immunol., Vol. 27, 1988, pp. 191–95. In combined treatment of degenerative diseases (such as rheumatoid arthritis, for example) the adsorbents include Chelex 100 and Staphylococcal Protein A, or matrix immobilized human IgG to bind the rheumatoid factor which is an autoantibody to IgG.

When whole blood is treated in the column, the optional plasma separation system is bypassed and the blood flows from vein 102A directly to column 106 via inlet 105. Optional membrane 113 and membrane 114 are permeable to blood cells and plasma, but not to adsorbent-bound matrix, which in this application when used in particle form utilizes particles in the range of 300–800 microns in diameter to ensure free flow of blood cells. The matrix can be in various other configurations such as fibers, membrane, capillaries, open porosity cavernous structure and the like. The matrix can be made of blood compatible synthetic polymer, natural polymer and silica as examples. The filter 134 may be made of smaller pore size when molecules smaller than LDL, such as free cholesterol, are to be removed. When LDL is removed, filter 134 is permeable to molecules the size of LDL but not larger molecules.

Figure 5:
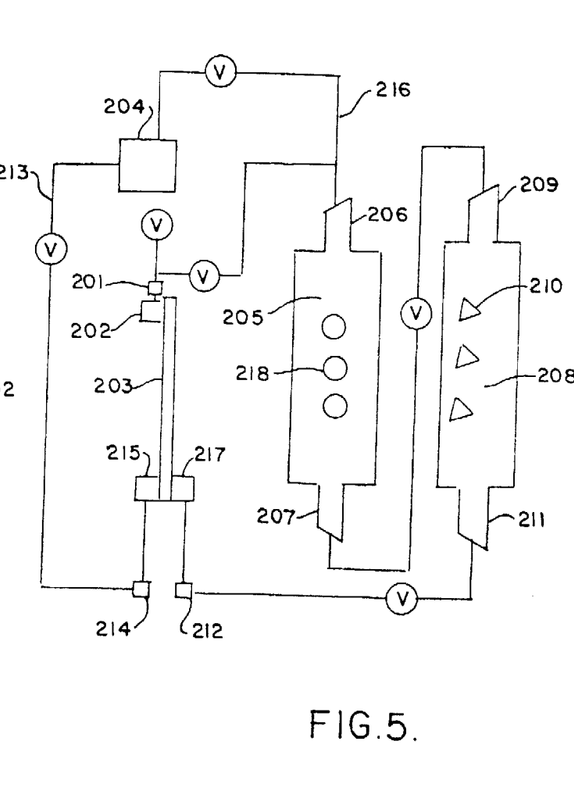
FIG. 5 is a diagrammatic view of two extracorporeal affinity adsorption devices connected in series for use in the present invention.

FIG. 5 illustrates the use of two or more devices, either filtration adsorption or direct adsorption when each of the specific adsorbents is contained in its own column. The devices and treatment process can be operated manually or automatically. One or more of the devices can be regenerated on line or off line. Either whole blood or plasma is adsorbed. Pumps as needed are included in the system to optimize fluid flow through the system. Pumps are also utilized as needed to increase trans-membrane pressure, when the filtration adsorption process is used.

Referring to FIG. 5, a catheter 201 is inserted in vein 202 of patient 203, optionally passed through continuous plasma cell separator 204 that is of either centrifugal or membrane type. The fluid (blood or plasma) is introduced into column 205 through inlet 206. Heavy metals in the fluid are adsorbed to Chelex 100 beads 218.

The fluid leaves column 205 via outlet 207. It has a significantly reduced content of heavy metals such as $Fe^{++}$ and $Cu^{++}$. The fluid is then introduced to column 208 via inlet 209. IgG and antibodies as well as antibody complexes are adsorbed on beads of Sepharose 4BCL/Protein A 210. Suitable filters are positioned in the columns as described in reference to FIG. 4. The fluid leaving through outlet 211 has a reduced level of antibodies and complexes. The fluid is returned to the patient via catheter 212 and vein 217. When the plasma cell separator is in use the cellular elements of the blood are returned to the patient via line 213, catheter 214 and vein 215.

Figure 6:
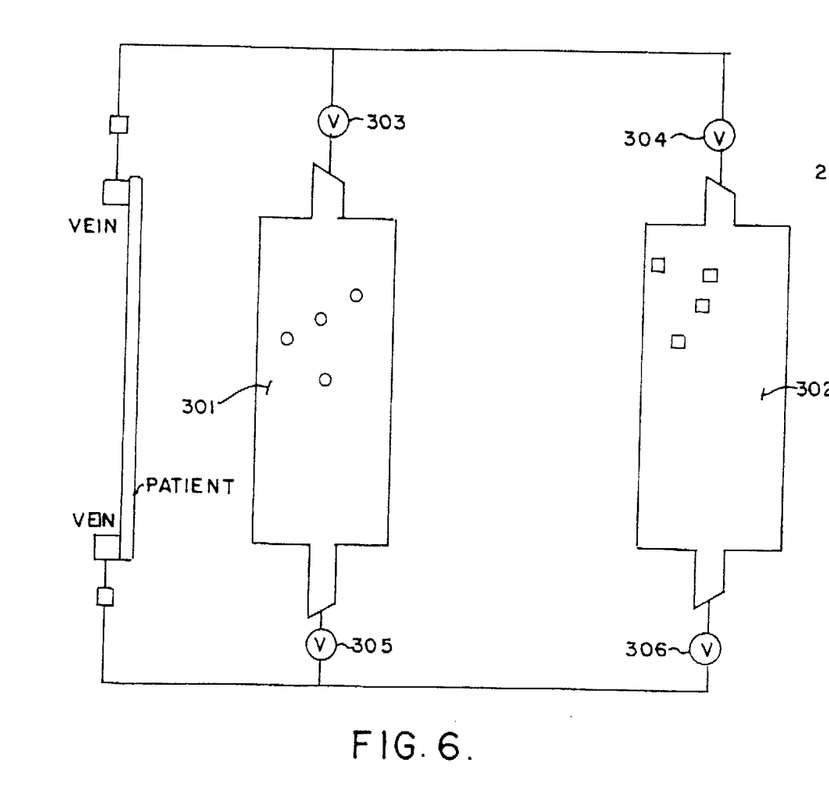
FIG. 6 is a diagrammatic view of two extracorporeal affinity adsorption devices connected in parallel for use in the present invention.

The columns can be connected to the patient in parallel, rather than consecutively, as illustrated in FIG. 6.

With either the manual or automatic operation of valving, the patient's blood or plasma can be transferred to column 301 and 302 either consecutively, with valve 303 open when valve 304 is closed and vice versa, or concurrently with valves 303 and 304 both open at the same time.

The method of Halbert, U.S. Pat. No. 4,637,880 may be used to regenerate one of two extracorporeal devices while the other device continues to be used, without removing either device from the mammal being treated, using any of the devices of the present invention.

In the utilization of the methods of the invention, with or without the optional on-line regeneration step, heparin or another suitable anticoagulant may be administered intravenously or into the device as required, as is well known to those skilled in the art of extracorporeal treatment. See for example, Bensinger, U.S. Pat. No. 4,614,513.

Particularly when no regeneration of adsorbents is utilized, other columns can replace columns described in the current invention. For example, the column of Kuroda et al., U.S. Pat. No. 4,627,915 can be used to adsorb IgG and immune complexes, and the column of Ambrus et al., U.S. Pat. No. 4,612,122 or can be used to remove heavy metals.

The present invention also includes the method of administering a drug bound (covalently or by other chemical binding) to an antibody such as an antibody specific to a tumor or to a tissue-specific antigen. Administration of the drug-antibody moiety is followed by a step of extracorporeally adsorbing the drug-hapten moiety by an antibody specific to the drug. The antibody in the extracorporeal device will thus adsorb both the drug-antibody moiety and the free drug in the circulation of the patient. The extracorporeal adsorption is preferably begun sufficiently long after the drug-antibody moiety is administered to permit the drug to reach a target in the mammal, although in some cases concurrent initiation of administration and adsorption is preferred. Generally, the time delay will typically be on the order of several minutes to forty-eight hours. An example of the drug is Adriamycin bound to a targeting antibody; the antibody in the extracorporeal specific affinity device will then be an antibody to Adriamycin. An example of the tissue specific antigens is thyroid gland specific antigen; an example of a tumor-specific antigen is human alpha-fetoprotein. Both the targeting antibody, to which the drug is initially bound, and the adsorbing antibody in the extracorporeal device may be an antibody fragment produced for example by synthesis or by enzymatic digestion treatment of a complete antibody. The adsorbent antibody is preferably linked to a matrix by a spacer arm of three to thirty carbon atoms; the targeting antibody is likewise preferably attached to the drug by a spacer. The adsorbing antibody may be made as a mirror image antibody, which binds to a site on the drug different from the site to which the targeting antibody is bound, by the method set out in my U.S. Pat. No. 4,375,414. Use of antibody to the drug in the extracorporeal device provides greater reduction in circulating drug (both bound and free), than does the antigen to which the targeting antibody is specific as used by Norrgren et al., supra.

Numerous other variations in the devices and methods of the present invention, within the scope of the appended claims, will occur to those skilled in the art in light of the foregoing disclosure.

I claim:

1. A method of treating atherosclerosis comprising a step of placing in an extracorporeal adsorption device at least one chelant which binds selectively with a metal ion oxidant, and a step of connecting the device in the blood circulatory system of a mammal to expose at least a portion of the blood of the mammal containing said metal ion to said chelant.

2. The method of claim 1 wherein the metal ion is selected from the group consisting of copper and iron.

3. The method of claim 1 wherein the adsorption device includes means for immobilizing said chelant on a matrix.

4. The method of claim 1 wherein the adsorption device is a pressure assisted filtration device including at least one semipermeable membrane.

5. The method of claim 4 wherein the semipermeable membrane is in the form of a hollow fiber.

6. The method of claim 5 wherein the semipermeable membrane comprises a plurality of hollow fibers.

7. A method of treating atherosclerosis comprising a step of placing in an extracorporeal affinity adsorption device at least two specific affinity adsorbents, one of said specific affinity adsorbents binding selectively with a first chemical species which is etiological to atherosclerosis and a second of said specific affinity adsorbents binding selectively with a second chemical species which is etiological to atherosclerosis, and a step of connecting the device in the blood circulatory system of a mammal to expose at least a portion of the blood of the mammal containing both said chemical species to said specific affinity adsorbents.

8. The method of claim 7 wherein the specific affinity adsorbents are prevented from entering the circulatory system by a semipermeable membrane.

9. An extracorporeal device for treating a disease state in a living mammal, the disease state being characterized by having a first chemical species comprising a metal ion oxidant etiological to the disease state or its symptoms and a second chemical species which is etiological to the disease state or to its symptoms, the device including means for drawing from the mammal a fluid containing the metal ion oxidant and the second chemical species, means for exposing the fluid to at least a first chelant binding means for chemically binding said metal ion oxidant in said device and to a second binding means for chemically binding said second chemical species in said device, and means for returning to the mammal at least a fraction of said fluid.

10. A method for treating a disease state in a living mammal, the disease state being characterized by having a first chemical species comprising a metal ion oxidant etiological to the disease state or its symptoms and a second chemical species which is etiological to the disease state or to its symptoms, the method comprising drawing from the mammal a fluid containing the metal ion oxidant and the second chemical species into an extracorporeal device, exposing the fluid to at least a chelant for chemically binding said first chemical species in said device, exposing the fluid to a specific affinity adsorbent for chemically binding said second chemical species in said device, and returning to the mammal at least a fraction of said fluid.

11. The method of claim 10 wherein the fluid is exposed simultaneously to the chelant and the specific affinity adsorbent.

12. The method of claim 10 wherein the fluid is exposed sequentially to the chelant and the specific affinity adsorbent.

13. The method of claim 1 wherein the specific affinity adsorbent binds immunologically.

14. The method of claim 1 wherein the disease state is atherosclerosis.

15. The method of claim 14 wherein the specific affinity adsorbent binds a chemical species selected from the group consisting of cholesterol, LDL, oxidized LDL, and antibodies to oxidized LDL.

16. The method of claim 10 wherein the disease state is autoimmune disease, and the specific affinity adsorbent binds a chemical species selected from the group consisting of autoantibodies and immune complexes.

17. The method of claim 16 wherein the specific affinity adsorbent binds immunologically.

18. The method of claim 10 wherein said specific affinity adsorbent is selected from the group consisting of Protein A, Protein G, and C1q bound to anti-C1q antibody.

19. The method of claim 10 wherein the disease state is cancer.

20. The method of claim 10 wherein said specific affinity adsorbent is a non-immunological chemical affinity adsorbent.

21. A method for treating a disease state in a living mammal, the disease state being characterized by having at least a first chemical species and a second chemical species which are etiological to the disease state or to its symptoms, the method comprising drawing from the mammal a fluid containing both the chemical species into an extracorporeal device, exposing the fluid to at least a first specific affinity adsorbent for chemically binding said first chemical species in said device, exposing the fluid to a second specific affinity adsorbent for chemically binding said second chemical species in said device, returning to the mammal at least a fraction of said fluid, and a further step of administering to the living mammal intravenously at least one plasma component.

22. The method of claim 21 wherein said plasma component is gamma globulin.

23. A method of treating atherosclerosis comprising a step of placing in an extracorporeal affinity adsorption device at least one chemical substance which binds selectively with autoantibodies to oxidized low density lipoproteins, and a step of connecting the device in the blood circulatory system of a mammal to expose at least a portion of the blood of the mammal containing autoantibodies to oxidized low density lipoproteins to said chemical substance.

24. The method of claim 23 wherein the chemical substance is selected from the group consisting of oxidized low density lipoprotein, Protein A, Protein G, and C1q bound to anti-C1q antibody.

25. An extracorporeal device including means for drawing from a mammal a fluid, chelant means in said device for exposing at least a portion of the fluid to a chelating agent for binding a metal ion and a specific affinity adsorbent in said device for chemically binding at least one chemical species in said fluid, and means for returning to the mammal at least a fraction of said fluid.

26. The device of claim 25 including a semipermeable membrane for preventing the specific affinity adsorbent from entering the body of the mammal.

27. The device of claim 26 wherein said fluid is blood, the device including means for attaching the device into the blood circulatory system of the mammal.

28. The device of claim 25 including at least two semipermeable membranes of different permeabilities.

29. The device of claim 25 wherein said at least a portion of said fluid is plasma.

30. The device of claim 25 including means for exposing the fluid simultaneously to the chelant and the specific affinity binding means.

31. The device of claim 25 including means for exposing said fluid sequentially to the chelant and the specific affinity binding means.

32. The device of claim 25 wherein the specific affinity binding means binds immunologically.

33. The device of claim 25 wherein said chelant binds a metal selected from the group consisting of iron and copper.

34. The device of claim 25 wherein the specific affinity binding means binds a species, selected from the group consisting of cholesterol, LDL, oxidized LDL and antibodies to oxidized LDL.

35. The device of claim 25 wherein the specific affinity binding means binds a chemical species selected from the group consisting of autoantibodies and immune complexes.

36. The device of claim 25 wherein the specific affinity binding means is selected from the group consisting of Protein A, Protein G, and C1q bound to anti-C1q antibody.

37. The device of claim 25 wherein the specific affinity binding means is a non-immunological chemical affinity adsorbent.

38. The device of claim 25 wherein the specific affinity binding means is an antibody to an anticancer drug or a fragment of such antibody.

39. The device of claim 38 wherein said drug is adriamycin.

40. The device of claim 25 wherein the specific affinity binding means binds to a moiety consisting of an anticancer drug and a targeting antibody chemically bound to said anticancer drug directly or through a spacer, said targeting antibody being an intact antibody or a fragment of an antibody.

41. The device of claim 40 in which said specific affinity binding means is an antibody specific to said drug in the drug-targeting antibody moiety or a fragment of such antibody.

42. The device of claim 40 wherein said specific affinity binding means is an antibody specific to a tumor or tissue targeting antibody in the drug-targeting antibody moiety, or a fragment of such antibody.

43. The device of claim 40 wherein said specific affinity binding means is tumor antigen or tissue antigen, or fetal antigen to which the targeting antibody is directed.

44. The device of claim 43 wherein said specific affinity binding means is human-alpha-fetoprotein.

45. The device of claim 40 wherein said drug in the anticancer drug targeting antibody moiety is adriamycin.

46. The device of claim 40 wherein said drug is radioactive.

47. A method for treating a disease state in a living mammal, the disease state being characterized by having at least a first chemical species and a second chemical species which are etiological to the disease state or to its symptoms, the method comprising drawing from the mammal a fluid containing both the chemical species into an extracorporeal device exposing the fluid to at least a first adsorbent for chemically binding the first chemical species in the device and to a second adsorbent for chemically binding the second chemical species in the device returning to the mammal at least a fraction of the fluid, and thereafter regenerating the device for further use by connecting a regenerating fluid to the device at least one of the adsorbents being a specific affinity adsorbent, the other adsorbent being a chelant.

48. The method of claim 47 wherein the fluid is exposed simultaneously to the specific affinity adsorbent and the chelant.

49. The method of claim 47 wherein the fluid is exposed sequentially to the specific affinity adsorbent and the chelant.

50. The method of claim 47 wherein the specific affinity adsorbent binds immunologically.

51. The method of claim 47 wherein the disease state is selected from the group consisting of rheumatoid arthritis and other autoimmune disease, and the specific affinity adsorbent binds a chemical species selected from the group consisting of autoantibodies and immune complexes.

52. The method of claim 47 wherein the specific affinity adsorbent is selected from the group consisting of Protein A, Protein G, and C1q bound to anti-C1q antibody.

53. The method of claim 47 wherein the specific affinity adsorbent is a non-immunological chemical affinity adsorbent.

54. A method for treating a disease state in a living mammal, the disease state being characterized by having at least a first chemical species and a second chemical species which are etiological to the disease state or to its symptoms, the method comprising drawing from the mammal a fluid containing both the chemical species into an extracorporeal device, exposing the fluid to at least a first adsorbent for chemically binding selectively with the first chemical species in the device and to a second adsorbent for chemically binding selectively with the second chemical species in the device, returning to the mammal at least a fraction of the fluid, and thereafter regenerating the device for further use by connecting a regenerating fluid to the device, wherein the disease state is atherosclerosis.

55. The method of claim 54 wherein one of the adsorbents binds selectively with a chemical species selected from the group consisting of cholesterol, LDL, oxidized LDL, and antibodies to oxidized LDL.

56. A method for treating a disease state in a living mammal, the disease state being characterized by having at least a first chemical species and a second chemical species which are etiological to the disease state or to its symptoms, the method comprising drawing from the mammal a fluid containing both the chemical species into an extracorporeal device, exposing the fluid to at least a first adsorbent for chemically binding the first chemical species in the device and to a second adsorbent for chemically binding the second chemical species in the device, returning to the mammal at least a fraction of the fluid, and thereafter regenerating the device for further use by connecting a regenerating fluid to the device, and a further step of administering to the living mammal intravenously at least one plasma component.

57. The method of claim 56 wherein the plasma component is gamma globulin.

58. A method of treating a disease state selected from the group consisting of cancer and autoimmune disease, the method comprising a step of placing in an extracorporeal adsorption device at least one chelant which binds selectively with a metal ion oxidant, and a step of connecting the device in the blood circulatory system of a mammal to expose at least a portion of the blood of the mammal containing said metal ion to said chelant.

59. The method of claim 58 wherein the disease state is cancer.

60. The method of claim 58 wherein the disease state is rheumatoid arthritis.

61. The method of claim 58 wherein the metal ion is selected from the group consisting of iron and copper.

62. A method of treating an autoimmune disease, the method comprising a step of placing in an extracorporeal adsorption device at least one chelant which binds selectively with a metal ion oxidant, and a step of connecting the device in the blood circulatory system of a mammal to expose at least a portion of the blood of the mammal containing said metal ion to said chelant.

* * * * *

UNITED STATES PATENT AND TRADEMARK OFFICE
CERTIFICATE OF CORRECTION

PATENT NO. : 5,753,227
DATED : May 19, 1998
INVENTOR(S) : Meir Strahilevitz

It is certified that error appears in the above-identified patent and that said Letters Patent is hereby corrected as shown below:

Col. 14, line 46
 replace "claim 1"
 with --claim 10--.

Col. 14, line 48
 replace "claim 1"
 with --claim 10--.

Signed and Sealed this

Eighth Day of September, 1998

Attest:

BRUCE LEHMAN

*Attesting Officer*     *Commissioner of Patents and Trademarks*